United States Patent [19]

Davidson

[11] Patent Number: Plant 7,442

[45] Date of Patent: Feb. 12, 1991

[54] ROSE PLANT NAMED WESTERN SUNLIGHT

[76] Inventor: Harvey D. Davidson, #3 El Verano Rd., Orinda, Calif. 94563

[21] Appl. No.: 457,145

[22] Filed: Dec. 26, 1989

[51] Int. Cl.[5] ..... A01H 5/00

[52] U.S. Cl. ..... Plt./16

[58] Field of Search ..... Plt. 16,17

*Primary Examiner*—James R. Feyrer

[57] ABSTRACT

A new rose variety of the hydrid tea class characterized by having high pointed flowers with apricot-orange inner petals and broad light orange outer petals which flex back with unusually fine form.

1 Drawing Sheet

1

The present invention relates to a new and distinctive variety of rose plant of the hybrid tea class, which was originated by my crossing ((Honey Favorite×Irish Mist)×(San Francisco×Prima Ballerina)) as the seed parent with Just Joey as the pollen parent.

Among the novel characteristics possessed by the new variety which distinguish it from its parents and all other varieties of which I am aware are:

(1) A flower with light orange outer petals deepening to apricot-orange inner petals with a very high pointed center during opening and having large broad petals which sequentially flex back with unusually fine form.

(2) Very rapid flowering cycles.

(3) Foliage with leaflets of distinctive perimeter serration.

(4) A vigorous upright plant of medium height.

Asexual reproduction of the new rose variety by budding, as performed at Waterdown, Ontario, Canada, shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in the color description herein refers to plate numbers in the aforementioned color chart, e.g. "53A" is plate "53A" of The Royal Horticultural Society Colour Chart.

American Rose Society Registration commercial appellation: "Western Sunlight".

Irar and Ciopora appellation: "Hadsun".

Parentage: Seedling.

*Seed parent.*—"((Honey Favorite×Irish Mist)×(San Francisco×Prima Ballerina))".

*Pollen parent.*—"Just Joey".

Class: Hybrid Tea.

The following observations are made of specimens grown outdoors in Contra Costa County, Calif., in the month of October.

2

FLOWER

Blooming habit:

A. Bud:

(1) *Size.*—Large.

(2) *Form.*—Pointed.

(3) *Sepals.*—30 to 37 mm in length; 10 to 12 mm extension beyond bud; 2 to 3 sepals show 20–23 edge appendages approximately 1 mm long with 1–2 appendages between 3–6 mm; heavy cotton matting on inner surface; fine light cover hairs on outer surface. Color before breaking — 144A; when turned down — 145A.

(4) *Peduncle.*—Length — 5 cm; Surface — smooth, no prickles or hairs; Strength — stiff, slight curvature. Color — 152C flushed 178B.

(5) *Color.*—When sepals first divide — outside petals 23A shading to 23B, inside petals 22B.

B. Bloom:

(1) *Size.*—Average when open — 15 cm.

(2) *Borne.*—Singly.

(3) *Form.*—Cupped, full, very high center remaining through maturity; petals curl back as bloom opens.

(4) *Petalage.*—Average number — 32.

(5) *Color.*—Early open — upper surface 27A shading to 22B; lower surface 29B. Aging — upper surface 23D, lower surface 24D.

C. Petals:

(1) *Texture.*—Thick.

(2) *Appearance.*—Satiny on both inside and outside.

(3) *Form.*—Broad, round, smooth edge.

(4) *Arrangement.*—Regular at all stages.

(5) *Petaloids in center.*—Average 2 to 3.

(6) *Persistence.*—Drop off cleanly.

(7) *Fragrance.*—Light fruit.

(8) *Lasting quality.*—Long lasting on bush; very good cut flower.

REPRODUCTION ORGANS

A. Stamen:

(1) *Arrangement.*—Regularly arranged around styles.

(2) *Number.*—Average — 180.

(3) *Length.*—Average 10–15 mm.

(4) *Filaments.*—Color — 45A.

(5) *Anthers.*—Color — 158A.

(6) *Pollen.*—23; viable.

Pistil:

(1) *Style.*—Covered with fine white hairs; color 51A; number 108–112.

(2) *Stigma.*—Color — 19A.

(3) *Ovary.*—To 11 mm diameter; to 6 cm depth.

C. Hips: Rarely sets seed.

(1) *Shape.*—Globular.

(2) *Color.*—22A.

(3) *Seed.*—Average 6 per hip, do not protrude.

PLANT

A. Form: Upright.

B. Growth: Vigorous. Medium height.—1 to 1.25 meters.

C. Foliage: Compound of 3 to 5 leaflets on bloom stem; 5 to 7 leaflets on main canes.

(1) *Size.*—Large.

(2) *Quantity.*—Stems well covered.

(3) *Color.*—New foliage upper side — 183A, under side — 178A. Old foliage — upper side 147A, under side — 147B.

(4) *Shape.*—Oblong to rounded with center pointed.

(5) *Texture.*—Upper side — leathery and glossy. Under side — smooth and dull.

(6) *Edge.*—Well defined noticeable serration on most of outer edge. Average 4 points per 1 cm, with up to 2 mm peak.

(7) *Rachis.*—Slight hair on upper side; smooth on lower side.

(8) *Stipules.*—Average length 3.5 to 4 cm; auricle to 8 mm.

D. Resistance to disease: Mildew and rust very good; Blackspot — none observed.

E. Wood:

*New wood.*—Color 178A; Bark — smooth.

*Old Wood.*—Color 148A, shading to areas of near 177A; Bark — smooth.

F. Thorns:

(1) *Thorns.*—Quantity: On main stalk many; on laterals from main stalk moderate. Form — Flat base, long pointed. Length — to 1 cm. Color — new 53A, aging to 181A. Position — irregular.

(2) *Prickles.*—None.

G. Winter hardiness: Good.

I claim:

1. A new and distinct variety of rose plant of the hybrid tea class, substantially as shown and described, characterized by its having large light orange to apricot colored single blooms with very high pointed centers and broad petals which sequentially flex back with unusually fine form; having rapid repeat bloom cycle and having glossy foliage with very distinctive serration on a vigorous disease resistant bush of moderate height.

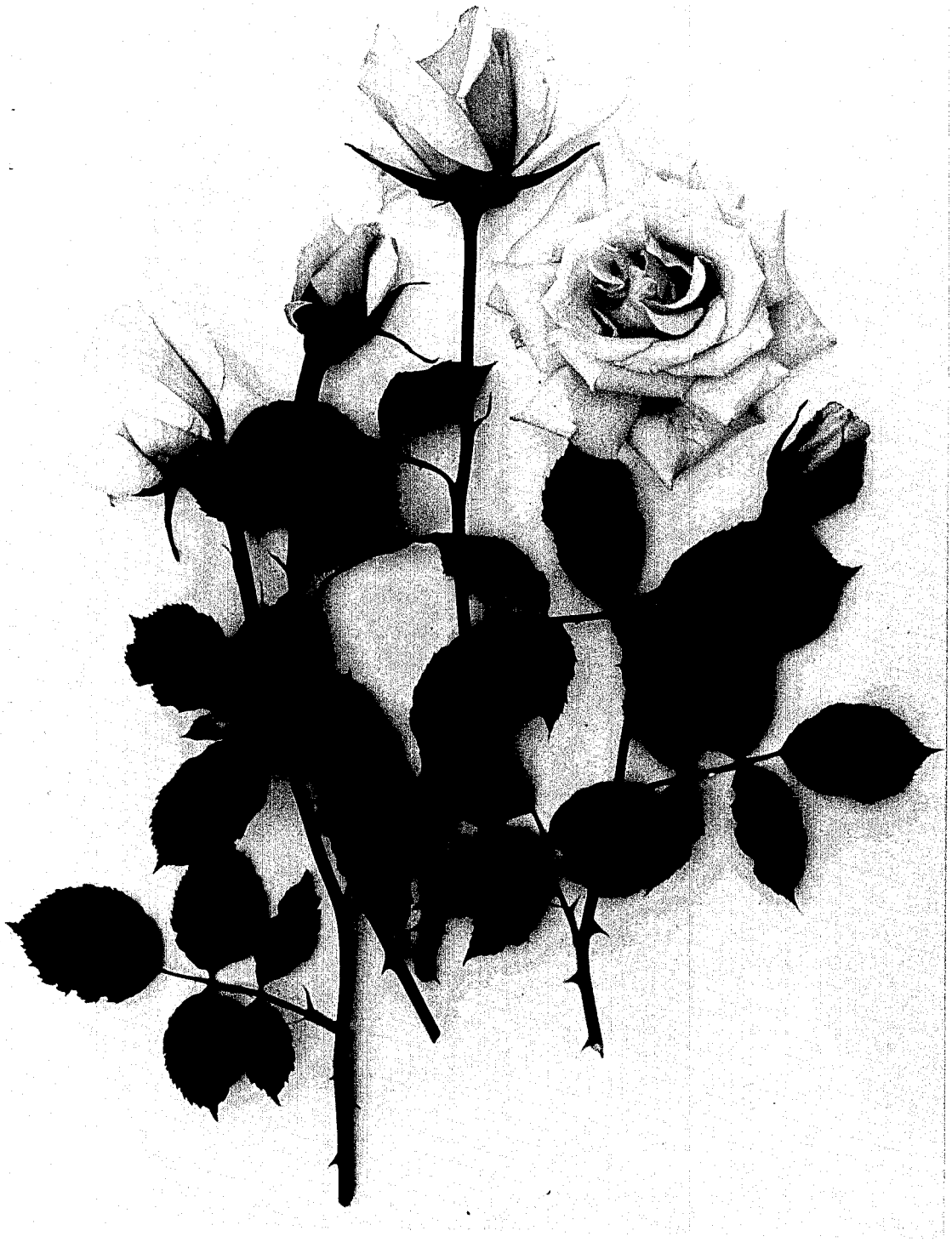

* * * * *